(12) United States Patent
Noda et al.

(10) Patent No.: US 11,635,806 B2
(45) Date of Patent: Apr. 25, 2023

(54) INFORMATION PROCESSING APPARATUS AND INFORMATION PROCESSING METHOD

(71) Applicant: SONY CORPORATION, Tokyo (JP)

(72) Inventors: Takuro Noda, Tokyo (JP); Kazuyuki Yamamoto, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/521,320

(22) Filed: Jul. 24, 2019

(65) Prior Publication Data

US 2019/0346920 A1 Nov. 14, 2019

Related U.S. Application Data

(63) Continuation of application No. 15/531,963, filed as application No. PCT/JP2015/075894 on Sep. 11, 2015, now Pat. No. 10,452,137.

(51) Int. Cl.
*G06T 7/73* (2017.01)
*G06T 11/60* (2006.01)
(Continued)

(52) U.S. Cl.
CPC ............ *G06F 3/013* (2013.01); *A61B 3/0091* (2013.01); *A61B 3/11* (2013.01); *A61B 3/113* (2013.01);
(Continued)

(58) Field of Classification Search
CPC ......... G06F 3/013; G06F 3/0346; G06T 7/73; G06T 11/60; G06T 2207/30204; A61B 3/0091; A61B 3/11; A61B 3/113
See application file for complete search history.

(56) References Cited

U.S. PATENT DOCUMENTS

2002/0176708 A1  11/2002  Irie
2003/0098954 A1   5/2003  Amir
(Continued)

FOREIGN PATENT DOCUMENTS

CN  102149325 A  8/2011
CN  102548465 A  7/2012
(Continued)

OTHER PUBLICATIONS

International Search Report and Written Opinion of PCT Application No. PCT/JP2015/075894, dated Nov. 24, 2015, 05 pages of English Translation and 05 pages of ISRWO.
(Continued)

*Primary Examiner* — Wing H Chow
(74) *Attorney, Agent, or Firm* — Chip Law Group

(57) ABSTRACT

An information processing apparatus capable of executing calibration for improving accuracy of gaze detection without causing a user to feel stress. The information processing apparatus, includes a marker control unit that changes, during calibration of an eyewear terminal, a display position of a point-of-regard marker displayed on a display unit of the eyewear terminal; a computational processing unit that computes an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and an evaluation unit that evaluates a variation of the optical axis vector computed for a plurality of the calibration points.

9 Claims, 12 Drawing Sheets

(51) Int. Cl.
  *G06F 3/01* (2006.01)
  *G06F 3/0346* (2013.01)
  *A61B 3/11* (2006.01)
  *A61B 3/113* (2006.01)
  *A61B 3/00* (2006.01)

(52) U.S. Cl.
  CPC .............. *G06F 3/0346* (2013.01); *G06T 7/73* (2017.01); *G06T 11/60* (2013.01); *G06T 2207/30204* (2013.01)

(56) References Cited

U.S. PATENT DOCUMENTS

| | | | |
|---|---|---|---|
| 2006/0110008 A1* | 5/2006 | Vertegaal | G06T 7/251 382/103 |
| 2006/0241900 A1 | 10/2006 | Hu et al. | |
| 2007/0279590 A1 | 12/2007 | Ebisawa | |
| 2009/0219484 A1 | 9/2009 | Ebisawa | |
| 2011/0214082 A1* | 9/2011 | Osterhout | G06F 1/1673 715/773 |
| 2011/0279666 A1 | 11/2011 | Strombom et al. | |
| 2013/0050642 A1 | 2/2013 | Lewis | |
| 2013/0050833 A1 | 2/2013 | Lewis | |
| 2013/0286178 A1 | 10/2013 | Lewis et al. | |
| 2014/0300538 A1 | 10/2014 | Rijnders | |
| 2015/0316981 A1* | 11/2015 | Sellen | G06K 9/0061 345/156 |
| 2016/0029883 A1* | 2/2016 | Cox | G06K 9/00604 351/209 |

FOREIGN PATENT DOCUMENTS

| | | |
|---|---|---|
| CN | 103353790 A | 10/2013 |
| CN | 103748598 A | 4/2014 |
| CN | 104063709 A | 9/2014 |
| JP | H07218858 A | 8/1995 |
| JP | 2002-345756 A | 12/2002 |
| JP | 2004-129927 A | 4/2004 |
| JP | 2005-245791 A | 9/2005 |
| JP | 2009297323 A | 12/2009 |
| JP | 2012068495 A | 4/2012 |
| JP | 2013190942 A | 9/2013 |
| JP | 2014-064634 A | 4/2014 |
| JP | 2014071811 A | 4/2014 |
| WO | WO-2005046465 A1 | 5/2005 |
| WO | 2006/108017 A2 | 10/2006 |
| WO | WO-2013078150 A1 | 5/2013 |

OTHER PUBLICATIONS

International Preliminary Report on Patentability of PCT Application No. PCT/JP2015/075894, dated Jun. 29, 2017, 06 pages of English Translation and 04 pages of IPRP.
Non-Final Office Action for U.S. Appl. No. 15/531,963, dated Nov. 29, 2018, 16 pages.
Notice of Allowance for U.S. Appl. No. 15/531,963, dated Apr. 25, 2019, 16 pages.
Office Action for CN Patent Application No. 201580067290.4, dated Aug. 1, 2019, 08 pages of Office Action and 10 pages of English Translation.
Office Action for KR Patent Application No. 10-2017-7013177, dated Feb. 26, 2022, 04 pages of English Translation and 04 pages of Office Action.

* cited by examiner

FIG.10
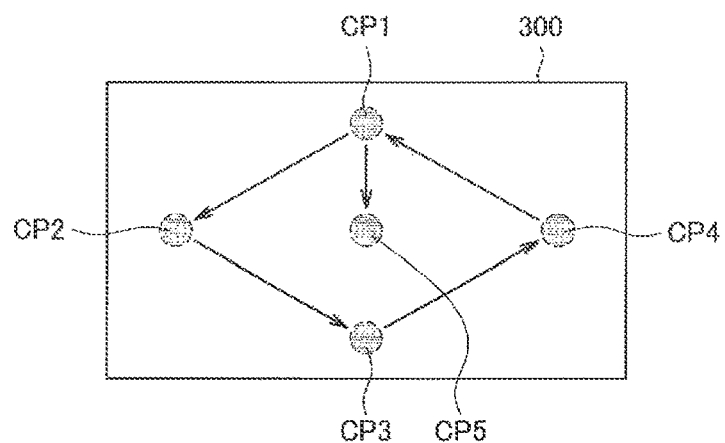
FIG.11
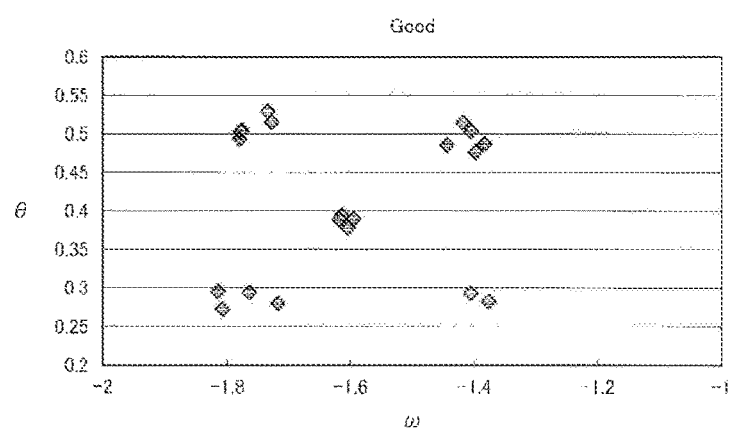
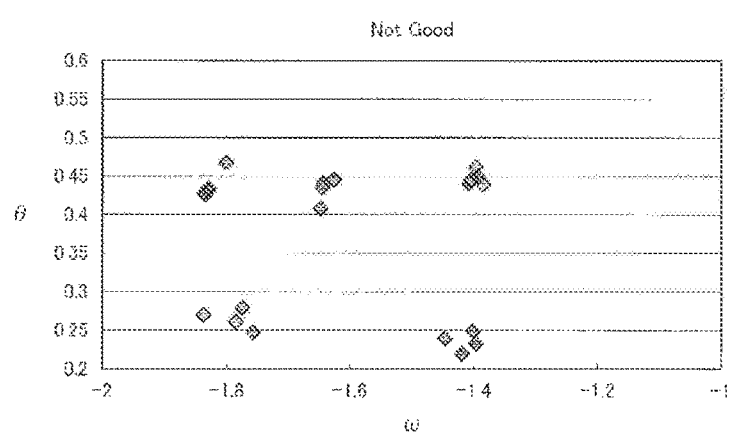

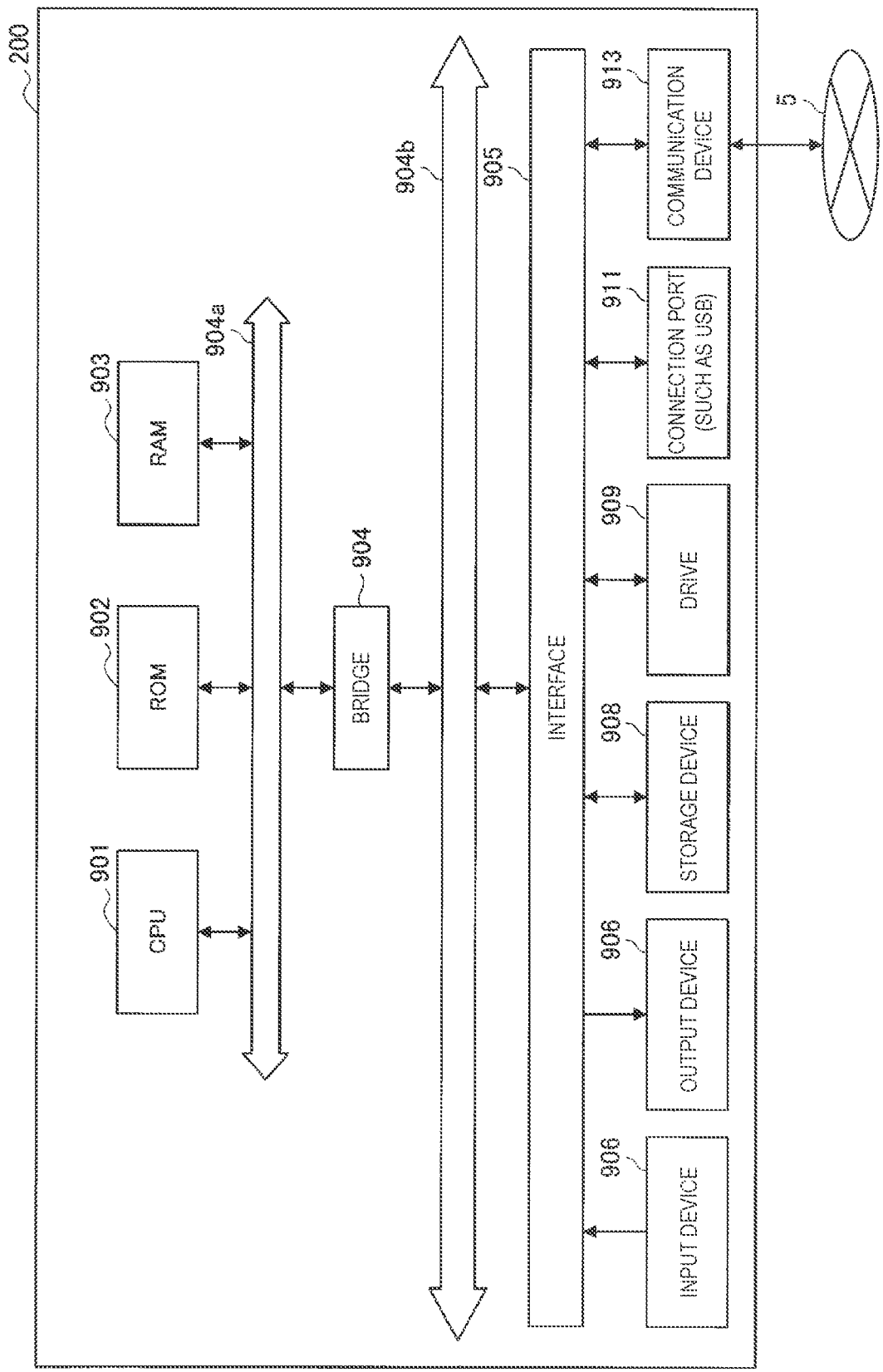

INFORMATION PROCESSING APPARATUS AND INFORMATION PROCESSING METHOD

CROSS-REFERENCE TO RELATED APPLICATION

The present application is a continuation application of U.S. patent application Ser. No. 15/531,963, filed May 31, 2017, which is a national stage entry of PCT/JP2015/075894, filed Sep. 11, 2015, which claims priority from prior Japanese Priority Patent Application JP 2014-254720 filed in the Japan Patent Office on Dec. 17, 2014, the entire contents of which are hereby incorporated by reference.

TECHNICAL FIELD

The present disclosure relates to an information processing apparatus, an information processing method, and a program.

BACKGROUND ART

There is disclosed technology that detects a user's gaze with respect to a display screen displaying a variety of content, and utilizes the detected gaze for various types of operations. For example, Patent Literature 1 discloses an imaging apparatus that radiates light in the infrared band (infrared light) onto the eye of a user peering into a viewfinder, and detects the user's gaze with respect to a display screen displaying a through-the-lens image by capturing the reflected light from the eye with a detector, and also utilizes the detected gaze for autofocus (AF).

CITATION LIST

Patent Literature

Patent Literature 1: JP H5-333259A

DISCLOSURE OF INVENTION

Technical Problem

Recently, the development of wearable terminals such as head-mounted displays and eyeglasses-style terminals has been advancing rapidly. Such technology that detects the user's gaze is also important in a wearable terminal worn by the user to view a display, and the detected gaze is used as terminal operation information, or used as autofocus information, for example. Particularly, in a wearable terminal, it is desirable to conduct calibration that improves the accuracy of gaze detection without causing the user to feel stress.

Accordingly, the present disclosure proposes a novel and improved information processing apparatus, information processing method, and program capable of executing calibration for improving the accuracy of gaze detection without causing the user to feel stress.

Solution to Problem

According to the present disclosure, there is provided an information processing apparatus, including: a marker control unit that changes, during calibration of an eyewear terminal, a display position of a point-of-regard marker displayed on a display unit of the eyewear terminal; a computational processing unit that computes an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and an evaluation unit that evaluates a variation of the optical axis vector computed for a plurality of the calibration points.

According to the present disclosure, there is provided an information processing method, conducted by an information processing apparatus, the method including: changing, during calibration of an eyewear terminal, a display position of a point-of-regard marker displayed on a display unit of the eyewear terminal; computing an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and evaluating a variation of the optical axis vector computed for a plurality of the calibration points.

According to the present disclosure, there is provided a program causing a computer to function as an information processing apparatus including: a marker control unit that changes, during calibration of an eyewear terminal, a display position of a point-of-regard marker displayed on a display unit of the eyewear terminal; a computational processing unit that computes an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and an evaluation unit that evaluates a variation of the optical axis vector computed for a plurality of the calibration points.

Advantageous Effects of Invention

According to the present disclosure as described above, it is possible to execute calibration for improving the accuracy of gaze detection without causing the user to feel stress. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 10 is an explanatory diagram illustrating another example of calibration points at which gaze data is acquired.

FIG. 11 is a graph illustrating an example of evaluation results of optical axis variation.

FIG. 15 is a hardware configuration diagram illustrating a hardware configuration of an information processing apparatus according to the embodiment.

MODE(S) FOR CARRYING OUT THE INVENTION

Figure 1:
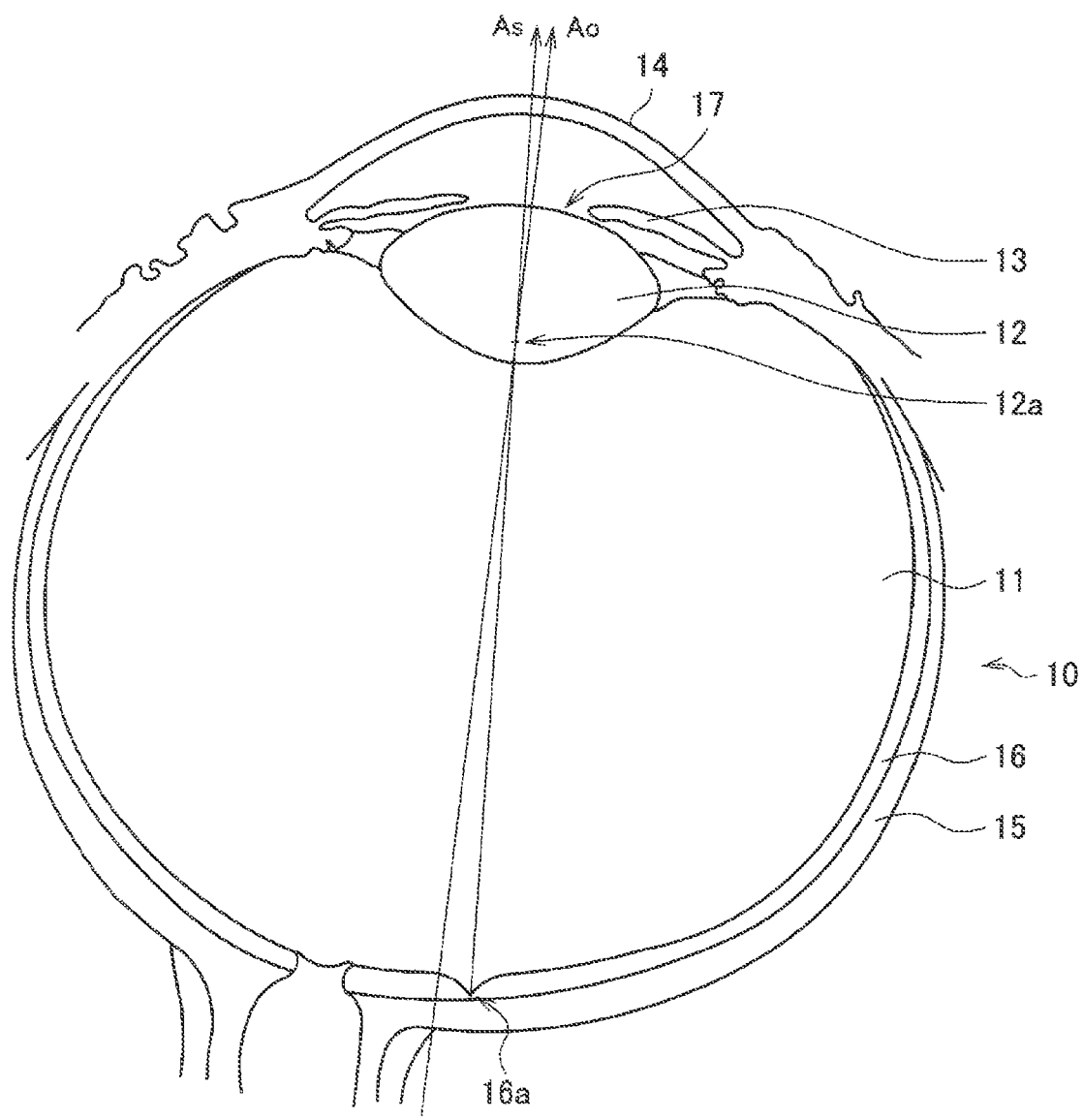
FIG. 1 is an explanatory diagram illustrating the structure of an eye.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. Overview
2. Hardware configuration of eyewear terminal
3. Functional configuration
4. Calibration process
(1) Display point-of-regard marker (S100)
(2) Acquire gaze data (S110 to S140)
(3) Evaluate (S150 to S180)
5. Adaptation to detection accuracy improvement
5.1. Pairing with bright points
5.2. Dynamic change of point-of-regard marker display position
6. Hardware configuration
<1. Overview>

First, an overview of an information processing apparatus according to an embodiment of the present disclosure will be described with reference to FIG. 1. Note that FIG. 1 is an explanatory diagram illustrating the structure of an eye.

An information processing apparatus according to the present embodiment is an apparatus that performs calibration executed to improve gaze detection accuracy when detecting the user's gaze with respect to a display. In the present embodiment, the user's gaze is detected using a pupil-corneal reflection method. The pupil-corneal reflection method is a technique that radiates light from a light source onto the user's eye, detects the reflected light from that light on the corneal surface and the position of the pupil, and estimates the gaze direction.

Herein, as illustrated in FIG. 1, the user's gaze lies on a sight axis As joining a node 12a on the central rear face of the crystalline lens 12 of the eye 10, and the fovea centralis 16a. Meanwhile, the gaze direction estimated by the above pupil-corneal reflection method lies on an optical axis Ao on the normal line of the cornea 14 that passes through the center of the pupil 17. A discrepancy exists between the sight axis As and the optical axis Ao, and although dependent on the individual, typically tends to range from approximately 4° to 8°. As this discrepancy becomes larger, gaze detection accuracy falls, and thus calibration is performed to correct this discrepancy.

The calibration is conducted according to the following procedure.
(Step 1) Estimate the optical axis when looking at a point inside the field of view (hereinafter also designated a "point-of-regard")
(Step 2) Measure the difference between the point-of-regard vector from the corneal center of curvature to the point-of-regard, and a vector of the estimated optical axis
(Step 3) On the basis of the difference measured in (Step 2), estimate the sight axis at the time from the optical axis when looking at an arbitrary point Note that since the eye 10 rotates by muscular pulling, a roll rotation is imparted depending on the direction in which to look. For this reason, the calibration parameter differs depending on the orientation of the eye 10. Accordingly, parameters ordinarily are acquired at multiple points of regard (for example, from 5 to 9 points) within the field of view.

With such calibration, error exists in the detection of reflected light from the pupil surface and the estimation of the optical axis. By moderating the variation of this error, it becomes possible to raise the accuracy of gaze detection. Accordingly, in an information processing apparatus according to the present embodiment, calibration is performed to moderate the variation of error. At this point, various processes are conducted so that calibration is executed without causing the user to feel stress. Hereinafter, the configuration and the functions of an information processing apparatus according to the present embodiment will be described in detail.

<2. Hardware Configuration of Eyewear Terminal>

Figure 2:
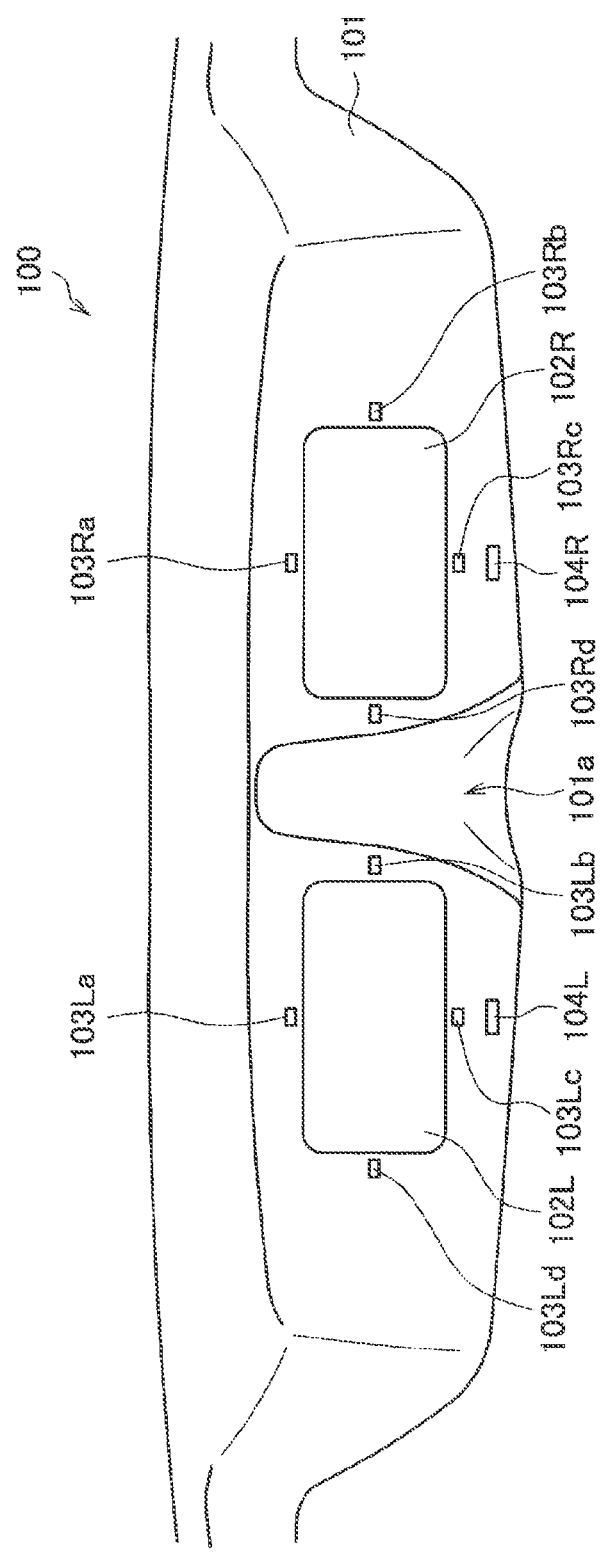
FIG. 2 is an explanatory diagram illustrating a configuration on the side facing the user's eyes in an eyewear terminal according to an embodiment of the present disclosure.
Figure 3:
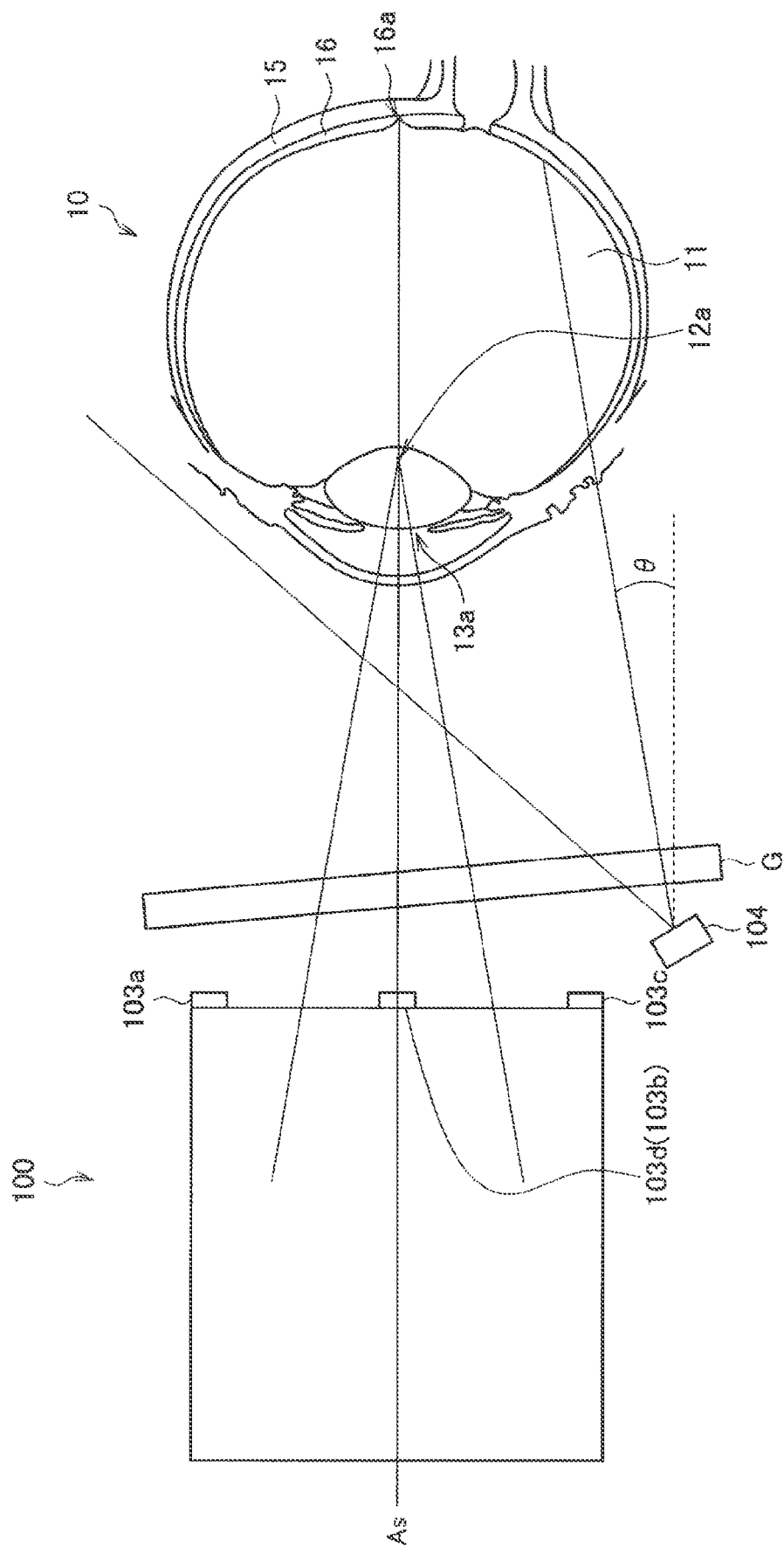
FIG. 3 is a schematic side view illustrating the positional relationship between the user's eye and an eyewear terminal when an eyewear terminal according to the embodiment is worn.

Prior to describing an information processing apparatus according to the present embodiment, a hardware configuration of an eyewear terminal 100 in which the calibration by the information processing apparatus according to the present embodiment is conducted will be described on the basis of FIGS. 2 and 3. Note that FIG. 2 is an explanatory diagram illustrating a configuration on the side facing the user's eyes in the eyewear terminal 100. FIG. 3 is a schematic side view illustrating the positional relationship between the user's eye 10 and the eyewear terminal 100 when the eyewear terminal 100 is worn.

The eyewear terminal 100 is a device which is worn on the user's head, and which is used in a state of the eyes facing one or more display units. The eyewear terminal 100 is a device such as a head-mounted display or an eyeglasses-style terminal, for example. As illustrated in FIG. 2, on the face on the side facing the user's eyes in the eyewear terminal 100 according to the present embodiment, respective display units 102R and 102L are provided at positions corresponding to the right eye and the left eye. The display units 102R and 102L according to the present embodiment are formed in an approximately rectangular shape. Note that on a housing 101, a depression 101a where the user's nose is positioned may also be formed between the display units 102R and 102L.

Around the perimeter of the display unit 102R, four light sources 103Ra, 103Rb, 103Rc, and 103Rd are respectively provided in the approximate middle of the four sides of the display unit 102R. Similarly, around the perimeter of the display unit 102L, four light sources 103La, 103Lb, 103Lc, and 103Ld are respectively provided in the approximate middle of the four sides of the display unit 102L. These light sources 103Ra to 103Rd and 103La to 103Ld are made up of a light source that emits infrared light. The light sources 103Ra to 103Rd and 103La to 103Ld radiate light onto the user's eye 10 that faces the display unit 102R or 102L around which the light sources are respectively provided.

Additionally, around the perimeter of the display units 102R and 102L, imaging unit 104R and 104L that capture an image of the eye 10 are provided, respectively. As illustrated in FIG. 2, for example, each of the imaging units 104R and 104L is provided under each of the display units 102R and 102L (below the light sources 103Rc and 103Lc provided under the display units 102R and 102L). As illustrated in FIG. 3, the imaging units 104R and 104L are disposed so that at least the pupil 17 of the eye 10 to capture is included in the capture range. For example, the imaging units 104R and 104L are disposed having a certain elevation angle θ. The elevation angle θ may be set to approximately 30°, for example.

Note that the eyewear terminal 100 is configured so that when worn by the user, the display units 102R and 102L are separated from the user's eyes 10 by a certain distance. Consequently, the user wearing the eyewear terminal 100 is able to keep the display regions of the display units 102R and 102L within his or her field of view without discomfort. At this point, the distance between the display units 102R and 102L and the user's eyes 10 may be decided so that even if the user is wearing glasses G, the eyewear terminal 100 is still wearable over the glasses G. In this state, the imaging units 104R and 104L are disposed so that the pupil 17 of the user's eye 10 is included in the capture range.

<3. Functional Configuration>

Next, a functional configuration of the eyewear terminal 100 discussed above and an information processing apparatus 200 that performs calibration of the eyewear terminal 100 will be described on the basis of FIG. 4. Note that FIG. 4 is a function block diagram illustrating a functional configuration of the eyewear terminal 100 and the information processing apparatus 200.

[3.1. Eyewear Terminal]

Figure 4:
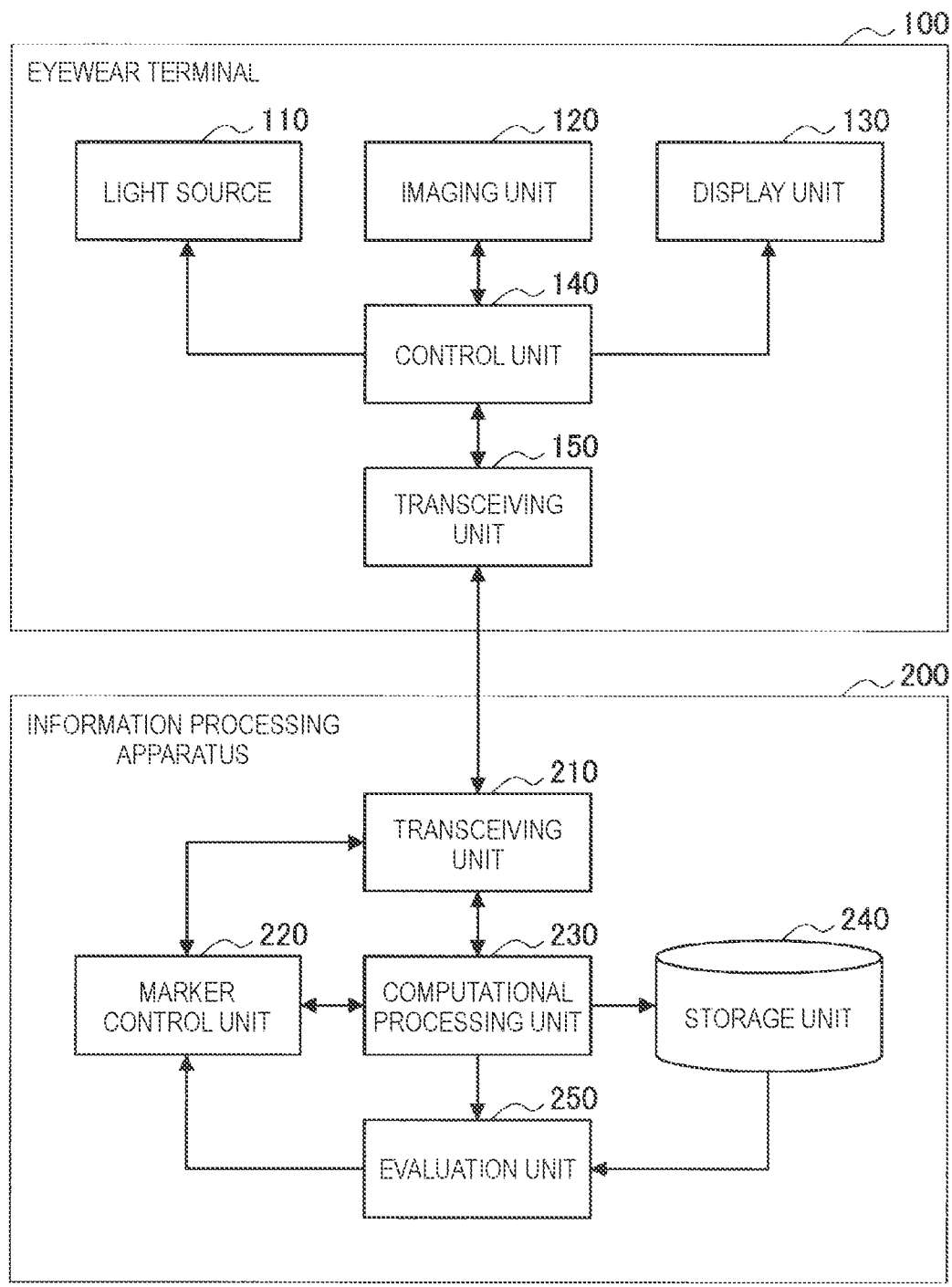
FIG. 4 is a function block diagram illustrating a functional configuration of an eyewear terminal and an information processing apparatus according to the embodiment.

As illustrated in FIG. 4, the eyewear terminal 100 is equipped with a light source 110, an imaging unit 120, a display unit 130, a control unit 140, and a transceiving unit 150.

The light source 110 radiates light on the eye 10 of a user wearing the eyewear terminal 100. The light source 110 is a light source that emits infrared light, for example, and corresponds to the light sources 103Ra to 103Rd and 103La to 103Ld in FIG. 2. The light source 110 emits light on the basis of an instruction from the control unit 140.

The imaging unit 120 captures the eye 10 of the user wearing the eyewear terminal 100. The imaging unit 120 corresponds to the imaging units 104R and 104L in FIG. 2. The imaging unit 120 conducts capture on the basis of an instruction from the control unit 140, and outputs a captured image to the control unit 140.

The display unit 130 is an output unit that displays information. The display unit 130 corresponds to the display units 102R and 102L in FIG. 2. The display unit 130 may be a liquid crystal display or an organic EL display, or alternatively, may be a lens on which information is displayed by a projection device, for example. Information is displayed on the display unit 130 according to an instruction from the control unit 140.

The control unit 140 controls the functions of the eyewear terminal 100 overall. The control unit 140 may perform control lighting control of the light source 110, perform capture control of the imaging unit 120, and display information on the display unit 130, for example. Additionally, the control unit 140 controls the transmission and reception of information to and from the information processing apparatus 200 via the transceiving unit 150.

The transceiving unit 150 is an interface that transmits and receives information to and from external equipment. In the present embodiment, calibration is conducted in the eyewear terminal 100 by transmitting and receiving information to and from the information processing apparatus 200. At this point, a captured image captured by the imaging unit 120 is transmitted from the eyewear terminal 100 to the information processing apparatus 200 via the transceiving unit 150. Also, information transmitted from the information processing apparatus 200, such as lighting control information for the light source 110 during calibration, capture control information causing the imaging unit 120 to perform capture, and display information causing the display unit 130 to display information, is received via the transceiving unit 150.

[3.2. Information Processing Apparatus]

Next, as illustrated in FIG. 4, the information processing apparatus 200 is equipped with a transceiving unit 210, a marker control unit 220, a computational processing unit 230, a storage unit 240, and an evaluation unit 250.

The transceiving unit 210 is an interface that transmits and receives information to and from external equipment. In the present embodiment, the transceiving unit 210 transmits and receives information for executing calibration to and from the eyewear terminal 100. At this point, the transceiving unit 210 transmits information, such as lighting control information for the light source 110 during calibration, capture control information causing the imaging unit 120 to perform capture, and display information causing the display unit 130 to display information, to the eyewear terminal 100. Additionally, the transceiving unit 210 receives information such as a captured image captured by the imaging unit 120 from the eyewear terminal 100.

The marker control unit 220 controls the display of a point-of-regard marker displayed on the display unit 130 of the eyewear terminal 100 during calibration. The point-of-regard marker is an object displayed in the display region to measure the discrepancy between the user's optical axis and sight axis. By causing the user to direct his or her gaze at the displayed point-of-regard marker, a vector from the user's pupil center to the point-of-regard marker (hereinafter also designated the "marker vector") may be obtained, and in addition, the user's optical axis at that time is also estimated.

The marker control unit 220 successively displays the point-of-regard marker at certain positions (hereinafter also designated "calibration points") so that the user's gaze data is acquired at multiple positions inside the display region. After a certain amount of gaze data is acquired at a calibration point where the point-of-regard is displayed, the marker control unit 220 repeats the process of moving the point-of-regard marker to the next calibration point, and acquires the user's gaze data at all calibration points.

At this point, the marker control unit 220 moves the point-of-regard marker between respective calibration points while keeping the point-of-regard marker displayed. As a result, the user's gaze moves to follow the point-of-regard marker, and compared to the case of intermittently displaying the point-of-regard marker, time to search for the point-of-regard marker displayed at a calibration point becomes unnecessary, and the movement of the gaze directed at the point-of-regard marker may be stabilized.

In addition, the marker control unit 220 may also control the movement speed of the point-of-regard marker moving between calibration points. If the point-of-regard marker is moved at a constant speed, the gaze tends to be less likely to settle down when the point-of-regard marker is displayed at the destination calibration point. Accordingly, the marker control unit 220 may control the movement speed of the point-of-regard marker moving between calibration points to slow down as the point-of-regard marker approaches the destination calibration point. Consequently, the point-of-regard marker moves quickly immediately after the start of movement, but slows down as the point-of-regard marker approaches the destination calibration point. Since the user's gaze moves along with the movement speed of the point-of-regard marker, the movement of the user's gaze also relaxes as the point-of-regard marker approaches the destination calibration point, and the gaze settles down more easily when the point-of-regard marker is dpisplayed at the calibration point.

The computational processing unit 230 respectively computes the user's optical axis and the marker vector when the point-of-regard marker is displayed at each calibration point. The computational processing unit 230 acquires from the eyewear terminal 100 a captured image depicting the user's eye regarding the point-of-regard marker while light from a light source is radiated onto the user's eyeball, and computes the user's optical axis and the marker vector. The computed optical axis and marker vector are stored in the storage unit 240 for each calibration point.

The storage unit 240 stores various information required during calibration of the eyewear terminal 100. For example, the storage unit 240 stores movement information stipulating the positions of calibration points at which to display the point-of-regard marker and how the point-of-regard marker is to move, and settings information such as the amount of gaze data to acquire at each calibration point and a threshold value used to determine the end of calibration. In addition, the storage unit 240 also stores gaze data computed by the computational processing unit 230.

The evaluation unit 250 determines the end of calibration of the eyewear terminal 100. The evaluation unit 250 determines whether or not the eyewear terminal 100 is correctly calibrated by determining whether or not the variation in the user's optical axis estimated at each calibration point is inside an allowed range. This determination process will be discussed in detail later. If the determination result from the evaluation unit 250 is that the variation in the user's optical axis is determined not to be contained inside a certain range, the calibration parameters are modified, and calibration is executed again.

The above thus describes a functional configuration of the eyewear terminal 100 and the information processing apparatus 200. Note that in FIG. 4, the information processing apparatus 200 that conducts the calibration process is illustrated as being separate from the eyewear terminal 100, but the present disclosure is not limited to such an example. For example, some or all of the functions of the information processing apparatus 200 illustrated in FIG. 3 may also be installed onboard the eyewear terminal 100.

<4. Calibration Process>

Figure 5:
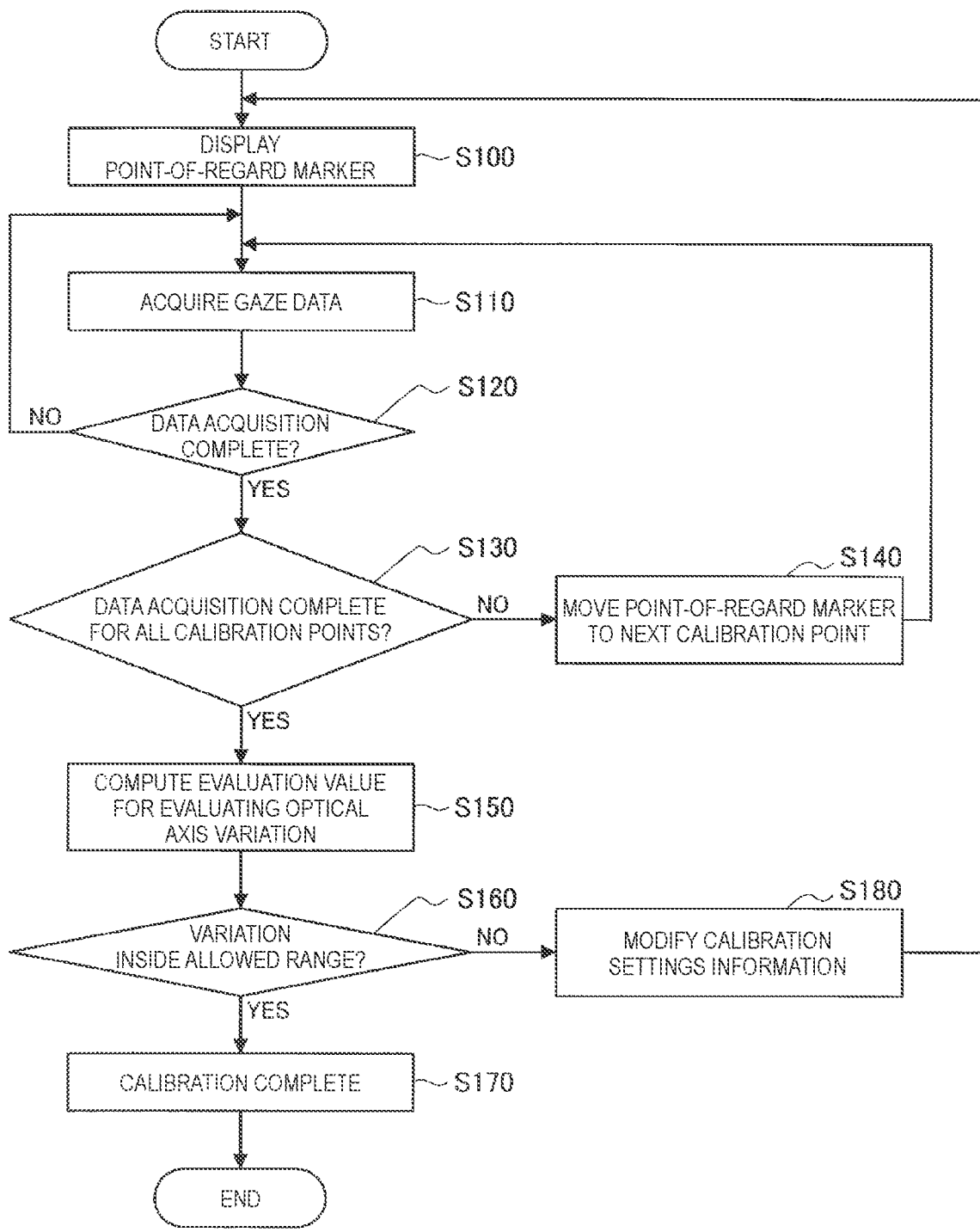
FIG. 5 is a flowchart illustrating a calibration process of an eyewear terminal performed by an information processing apparatus according to an embodiment.
Figure 6:
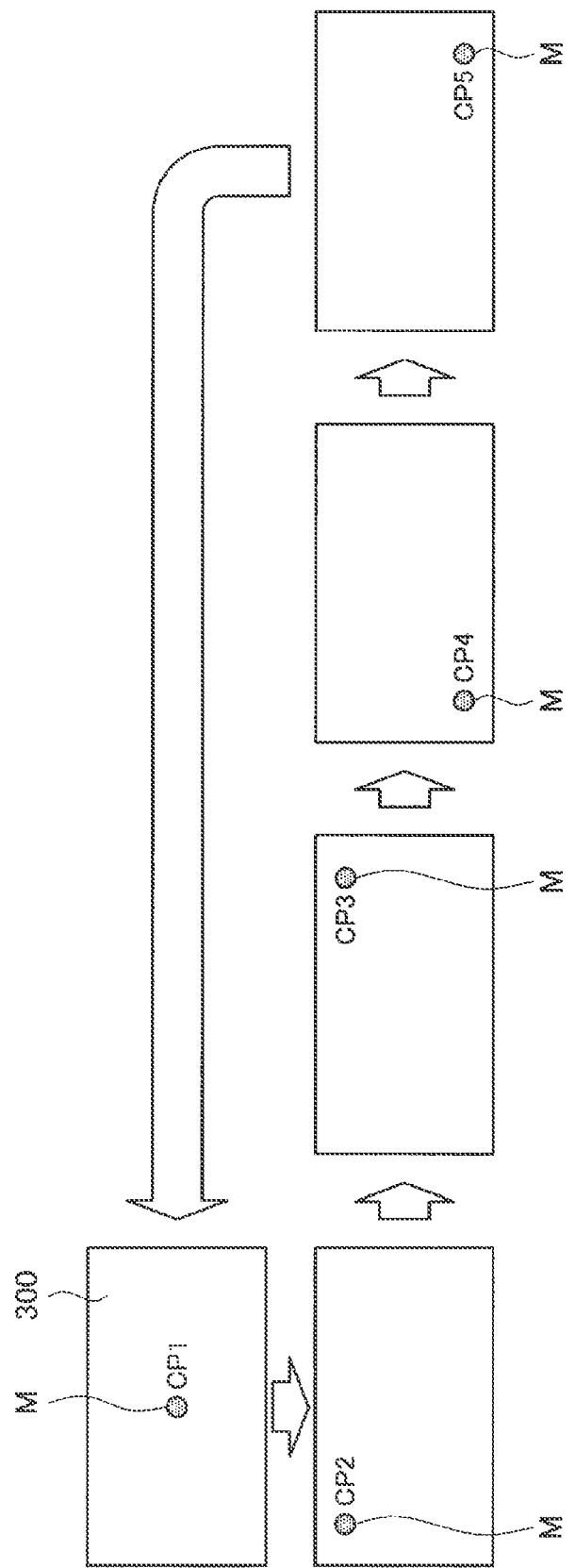
FIG. 6 is an explanatory diagram illustrating an example display of a point-of-regard that is displayed moving.
Figure 7:
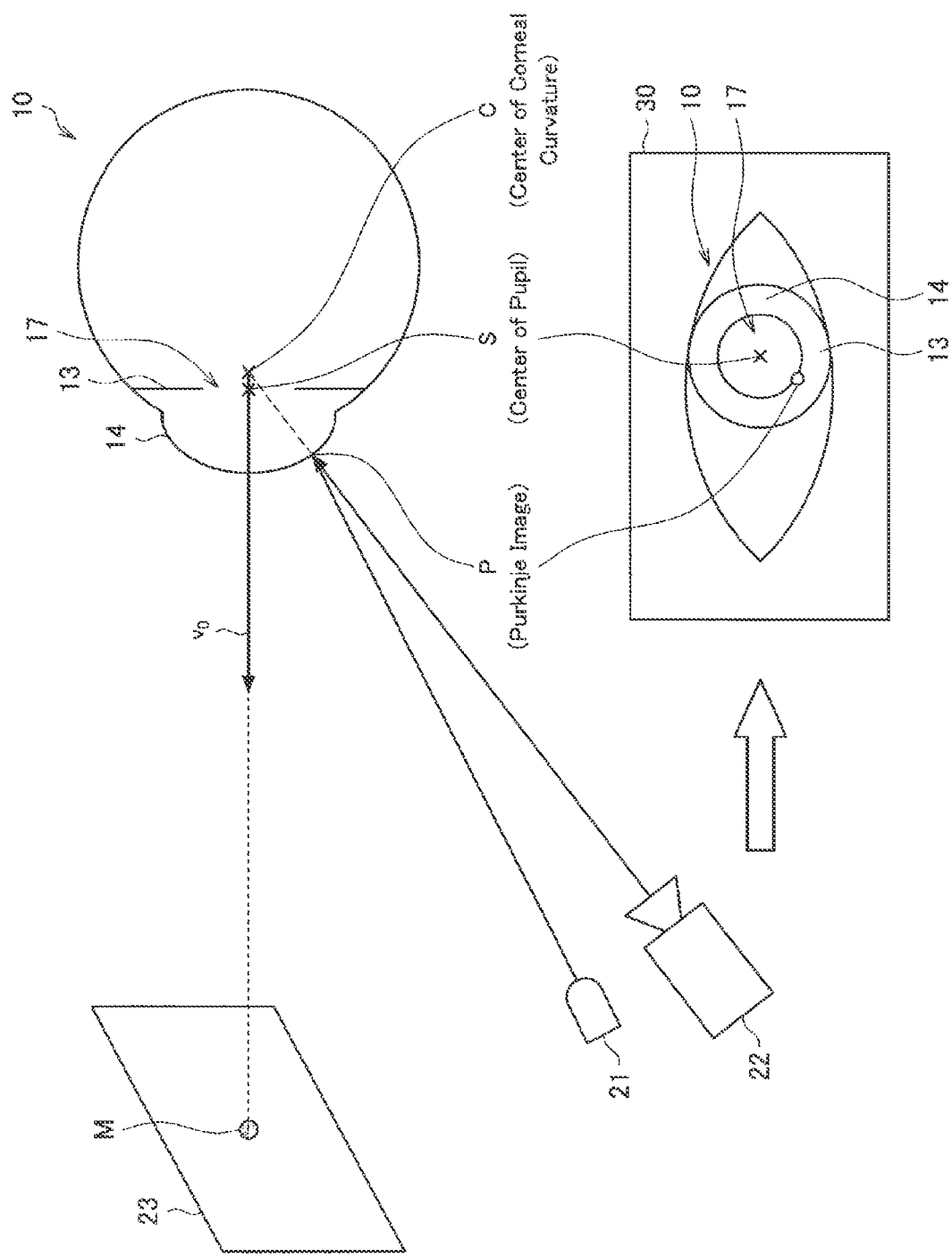
FIG. 7 is an explanatory diagram for explaining a process of computing an optical axis vector using a pupil-corneal reflection method.
Figure 8:
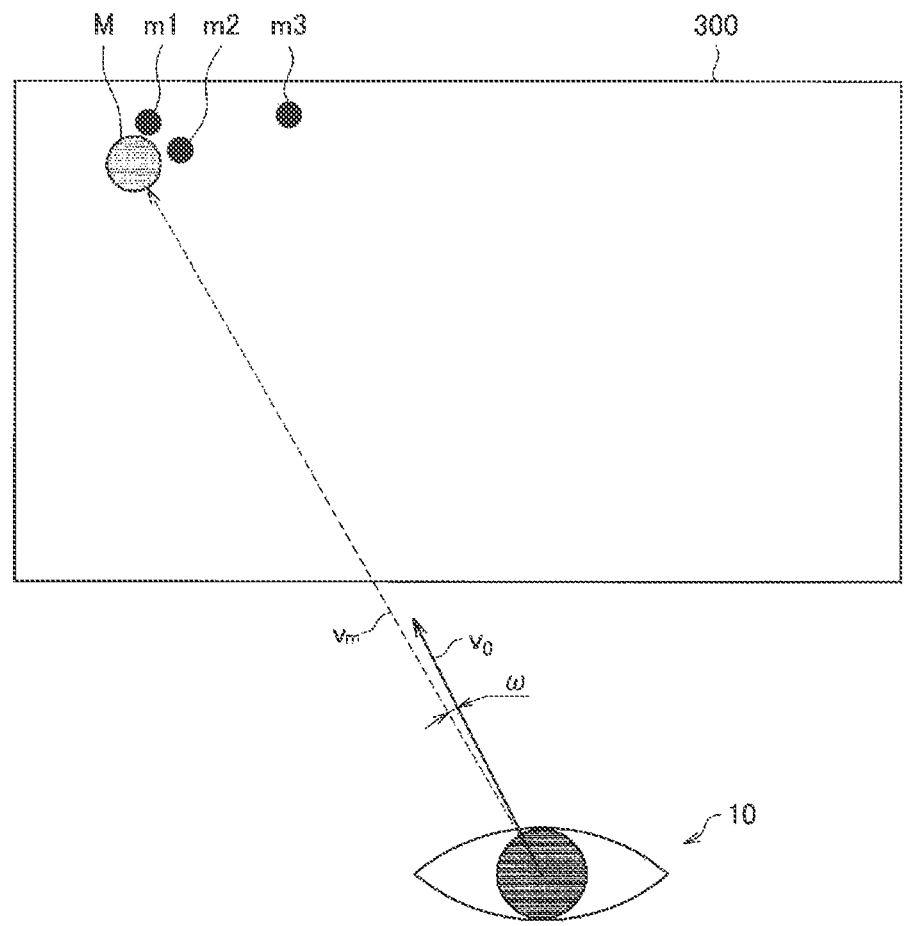
FIG. 8 is an explanatory diagram illustrating a relationship between a marker vector and an optical axis vector.
Figure 9:
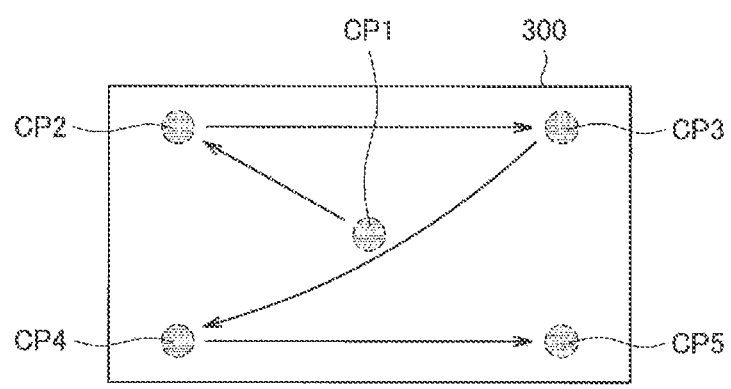
FIG. 9 is an explanatory diagram illustrating an example of calibration points at which gaze data is acquired.
Figure 12:
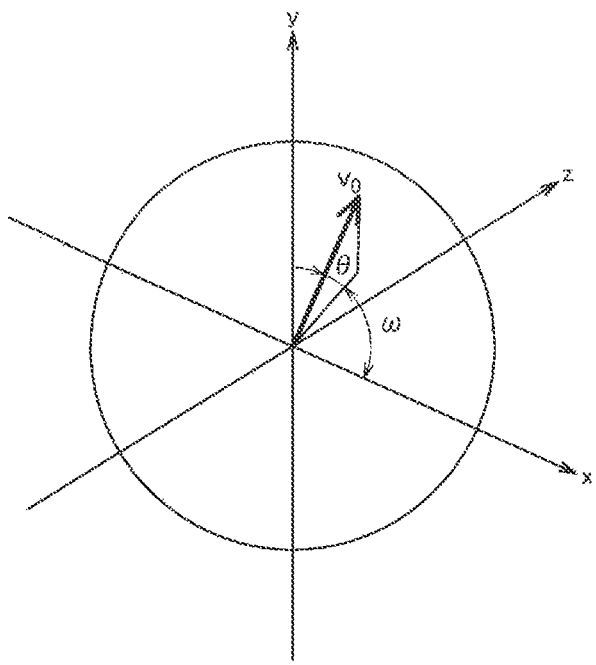
FIG. 12 is an explanatory diagram illustrating coordinates of a marker vector and an optical axis vector.
Figure 13:
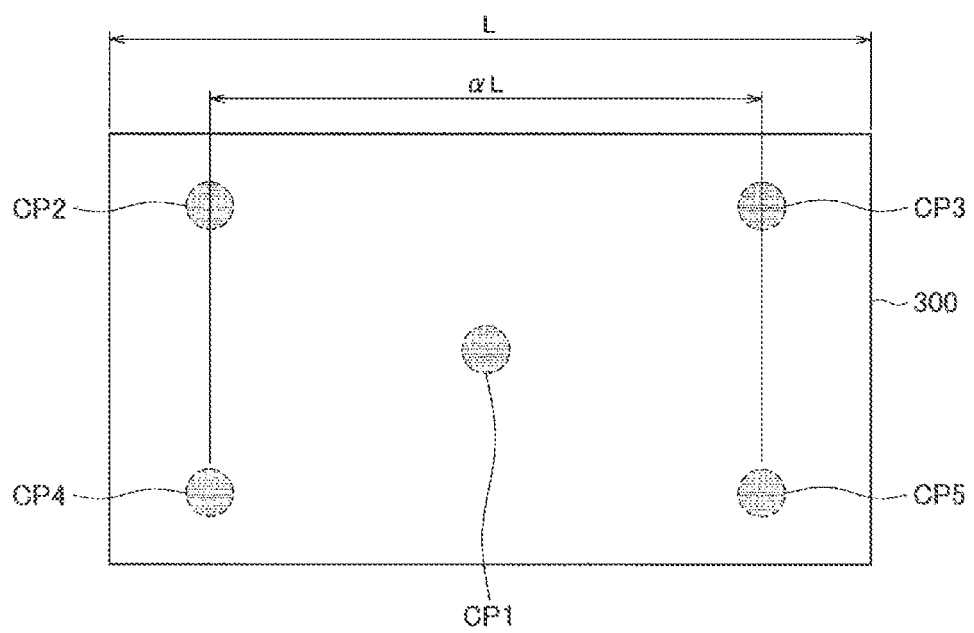
FIG. 13 is an explanatory diagram for explaining the modification of the positions of calibration points.
Figure 14:
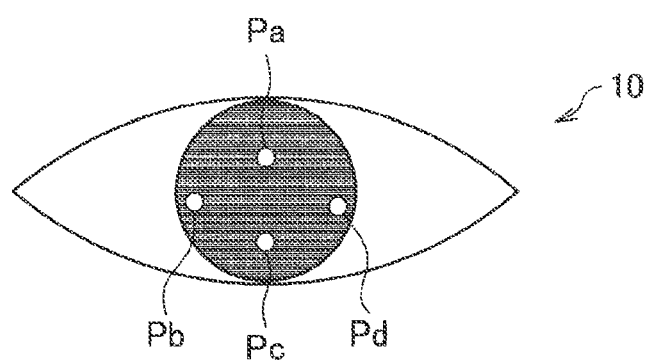
FIG. 14 is an explanatory diagram illustrating an example of bright points appearing on the eye when light is radiated from a light source.

Next, the calibration process of the eyewear terminal 100 performed by the information processing apparatus 200 according to the present embodiment will be described on the basis of FIGS. 5 to 14. Note that FIG. 5 is a flowchart illustrating the calibration process of the eyewear terminal 100 performed by the information processing apparatus 200 according to the present embodiment. FIG. 6 is an explanatory diagram illustrating an example display of a point-of-regard that is displayed moving. FIG. 7 is an explanatory diagram for explaining a process of computing an optical axis vector using a pupil-corneal reflection method. FIG. 8 is an explanatory diagram illustrating a relationship between a marker vector and an optical axis vector. FIG. 9 is an explanatory diagram illustrating an example of calibration points at which gaze data is acquired. FIG. 10 is an explanatory diagram illustrating another example of calibration points at which gaze data is acquired. FIG. 11 is a graph illustrating an example of evaluation results of optical axis variation. FIG. 12 is an explanatory diagram illustrating coordinates of a marker vector and an optical axis vector. FIG. 13 is an explanatory diagram for explaining the modification of the positions of calibration points. FIG. 14 is an explanatory diagram illustrating an example of bright points appearing on the eye when light is radiated from a light source.

(1) Display Point-of-Regard Marker (S100)

The calibration process of the eyewear terminal 100 performed by the information processing apparatus 200 according to the present embodiment starts by displaying the point-of-regard on the display unit 130, and causing the user to direct his or her gaze at the point-of-regard marker (S100). The display control of the point-of-regard marker is conducted by the control unit 140, which receives instructions from the marker control unit 220 of the information processing apparatus 200. In the calibration, the user's gaze data is acquired at multiple positions inside the display region of the display unit 130. By displaying the point-of-regard marker at a calibration point that acts as a position at which to acquire gaze data, the user intentionally directs his or her gaze at the point-of-regard marker, making it possible to acquire gaze data.

The point-of-regard marker is successively displayed at multiple preset calibration points inside the display region 300 of the display unit 130. As illustrated in FIG. 6, for example, the point-of-regard marker first is displayed at a calibration point CP1 in the center of the display region 300. When the point-of-regard marker M is displayed at the calibration point CP1, the user directs his or her gaze at the point-of-regard marker M. By keeping the point-of-regard marker M displayed, the user's gaze may be fixed on the calibration point CP1, and gaze data is acquired in this state.

After gaze data is acquired at the calibration point CP1, the point-of-regard marker M, while still being displayed, is moved to the next position at which to acquire gaze data, namely the calibration point CP2 in the upper-left of the display region 300. Subsequently, gaze data at the calibration point CP2 is acquired. After that, the acquisition of gaze data and the movement are repeated for the calibration point CP3 at the upper-right of the display region 300, at the calibration point CP4 at the lower-left of the display region 300, and the calibration point CP5 at the lower-right of the display region 300. In step S100, the point-of-regard marker M is displayed at the first calibration point, and the calibration process is started.

(2) Acquire Gaze Data (S110 to S140)

After the point-of-regard marker M is displayed at the first calibration point in step S100, the user's gaze data at that calibration point is acquired (S110). The gaze data includes an optical axis vector expressing the estimated gaze direction of the user, and a marker vector from the user's pupil center to the point-of-regard marker.

(Computation of Optical Axis Vector)

The optical axis vector is estimated using the pupil-corneal reflection method, for example. A process of estimating the optical axis using the pupil-corneal reflection method will now be described on the basis of FIG. 7. In the pupil-corneal reflection method, light from a light source 21 is radiated onto the eye 10 of the user observing the display screen 23 of the display unit, and the eye 10 irradiated by the light is imaged by an imaging unit 22. Subsequently, the optical axis is estimated on the basis of a captured image 30 imaged by the imaging unit 22. For the sake of simplicity, the case of irradiating the eye 10 with one light source 21 will be described herein.

As illustrated in FIG. 7, suppose that the user is regarding the point-of-regard marker M displayed on the display screen 23. At this point, the eye 10 is irradiated with light from the light source 21, and the eye 10 is imaged by the imaging unit 22. As illustrated in FIG. 7, the acquired captured image 30 of the eye 10 depicts the cornea 14, the iris 13, and the pupil 17 of the user's eye 10. The captured image 30 also depicts a Purkinje image P, which is a bright point of irradiating light irradiating the eye 10 from the light source 21.

After the captured image 30 is acquired, a process of computing the optical axis is conducted. The process of computing the optical axis is conducted by the computational processing unit 230. For this reason, first, the pupil center S and the Purkinje image P are detected from the captured image 30. These detection processes may be conducted by known image recognition technology.

For example, in the process of detecting the image of the pupil 17, various types of image processing with respect to the captured image 30 (for example, processing to adjust factors such as distortion, black level, and white balance), a process of acquiring a luminance distribution inside the captured image 30, and the like are conducted. Also, on the basis of the acquired luminance distribution, a process of detecting an edge in the image of the pupil 17, a process of approximating the detected edge in the image of the pupil 17 with a figure such as a circle or an ellipse, and the like may be conducted. From the detected image of the pupil 17, the pupil center S may be computed.

Additionally, in the process of detecting the Purkinje image P, a series of processes, such as the various types of image processing with respect to the captured image 30, the process of acquiring a luminance distribution inside the captured image 30, and a process of detecting pixels where the difference in the luminance value is comparatively larger than the surrounding pixels on the basis of the luminance distribution, may also be conducted. Also, the center of the Purkinje image P may be detected from the detected Purkinje image P.

Next, three-dimensional coordinates of the pupil center S and a curvature center C of the cornea 14 are computed. When the cornea 14 is taken to be part of a sphere, the curvature center C of the cornea 14 is the center of the sphere. The three-dimensional coordinates of the pupil center S are computed on the basis of the image of the pupil 17 detected from the captured image 30. Specifically, the three-dimensional coordinates of each point on the edge of the pupil 17 in the captured image 30 are computed on the basis of properties such as the positional relationship between the imaging unit 22 and the eye 10, the refraction of light at the surface of the cornea 14, and the distance between the curvature center C of the cornea 14 and the pupil center S. The center point of these coordinates is taken to be the three-dimensional coordinates of the pupil center S.

In addition, the curvature center C of the cornea 14 is computed on the basis of the Purkinje image P and the center thereof detected from the captured image 30. Specifically, on a straight line joining the imaging unit 22 and the center of the Purkinje image P, the position advanced from the surface of the cornea 14 inward into the eye 10 by the curvature radius of the cornea 14 is computed as the three-dimensional coordinates of the curvature center C of the cornea 14, on the basis of properties such as the positional relationship between the light source 21, the imaging unit 22, and the eye 10, and the curvature radius of the cornea 14.

The straight line joining the curvature center C of the cornea 14 computed in this way and the pupil center S becomes the estimated optical axis. In other words, the coordinates of the position at which the optical axis and the display screen 23 intersect become the estimated gaze position of the user. Note that a vector proceeding from the curvature center C of the cornea 14 to the pupil center S is designated the optical axis vector vo.

(Computation of Marker Vector)

Meanwhile, the marker vector from the user's pupil center S to the point-of-regard marker M may be computed as the vector proceeding from the pupil center S specified from the captured image 30 as discussed above to the position on the display screen 23 where the point-of-regard marker M is displayed currently.

In this way, in step S110, the optical axis vector and the marker vector are computed and acquired by the computational processing unit 230 as gaze data. The acquired gaze data is stored in the storage unit 240.

(Moderating Variation in Detection Results)

At this point, the computational processing unit 230 may also determine whether or not the computed optical axis vector vo is usable as a calibration detection result.

Specifically, for example, the computational processing unit 230 may determine whether or not wobbling of the optical axis vector vo is within a certain range, and confirm that the computed optical axis vector vo is not greatly divergent from the optical axis vectors vo acquired so far. Optical axis vectors vo computed by the computational processing unit 230 are stored as a history in the storage unit 240. Using this history, the computational processing unit 230 confirms that the angle obtained between an average vo_ave of the previous N acquired optical axis vectors, including the current computation, and the current optical axis vector vo is inside a certain value, for example. Additionally, when the angle obtained between the optical axis vector average vo_ave and the current optical axis vector vo exceeds a certain threshold value, the currently computed optical axis vector vo is treated as a large wobble, and is not used as a calibration detection result. As a result, the accuracy of the optical axis vector may be increased.

The optical axis vector average vo_ave may be computed using the previous three optical axis vectors vo, for example. Also, the threshold value for determining the angle obtained between the optical axis vector average vo_ave and the current optical axis vector vo may be set to approximately 3°, for example. This threshold value is decided while accounting for the inconsistency of detection. According to such a determination, when given the estimated user gaze positions m1, m2, and m3 as illustrated in FIG. 8, for example, a point like the gaze position m3 which is divergent from the others may be excluded from the detection results. Additionally, even if the optical axis vector vo is computed from a captured image that is imaged when the user is not looking at the point-of-regard marker M, the computed optical axis vector vo becomes greatly divergent from the optical axis vector average vo_ave. The optical axis vector vo in such a case may also be excluded from the detection results by the determination.

In addition, the computational processing unit 230 may also determine whether or not an angle w obtained between the computed marker vector vm and the optical axis vector vo is less than or equal to a certain value, for example. According to such a determination, it is possible to confirm whether the estimated optical axis vector vo is greatly divergent from the actual gaze direction. The value of the threshold used at this point is decided with consideration for factors such as the discrepancy between the optical axis and the sight axis, and the optical axis detection error.

For example, the estimated gaze direction of the user (in other words, the optical axis) and the direction in which the user actually is looking (in other words, the sight axis) do not necessarily match. This is due to factors such as the shape and size of the eyeball, and the arrangement of the retina and optic nerve in the eyeball. Although there is individual variation, the discrepancy between the optical axis and the sight axis ordinarily is from 4° to 8°. Also, an optical axis detection error of several degrees, such as up to ±3°, for example, is considered to exist. If this error is combined with other accumulative error of ±1°, an error ranging approximately from 0° to 12° is anticipated to occur. In this case, if the angle w obtained between the computed marker vector and the optical axis vector is inside the range from 0° to 12°, the computed optical axis vector vo may be treated as being of allowable accuracy, and may be used as a calibration detection result.

By conducting such a determination process, variation in the detection results may be moderated, and the accuracy of the optical axis vector may be increased.

(Misdetection Determination)

Furthermore, even if detection clears the above determination for moderating variation in the detection results, the pupil or the bright point may be continually detected at an incorrect location in some cases. If an incorrect detection result is used, the calibration process cannot be conducted correctly. Accordingly, the computational processing unit 230 may also conduct a misdetection determination process so as not to use such an incorrect detection result as a calibration detection result. For example, if the computed sizes of the left and right pupils are extremely different, there is a strong possibility that an incorrect location may be recognized as a pupil. The gaze data acquired in such a case is not used as a detection result. As a specific example, if the size ratio of the left and right pupils exceeds a certain value (for example, 1.2), the sizes of the left and right pupils may be treated as being extremely different, and the acquired gaze data may not be used as a detection result.

After the above processes are conducted, the computational processing unit 230 determines whether or not gaze data has been acquired at the calibration point where the point-of-regard marker M is displayed currently (S120). For example, if a correct result has not been obtained, such as when wobbling is determined to exist in the optical axis vector vo from past data, or when the angle w obtained between the marker vector vm and the optical axis vector vo is not inside the allowed range, the eye 10 is imaged and gaze data is acquired again.

Meanwhile, when gaze data is acquired at the calibration point where the point-of-regard marker M is displayed currently, the computational processing unit 230 determines whether or not gaze data has been acquired for all calibration points (S130). The calibration points at which to acquire gaze data are stored in advance in the storage unit 240. If there exists a calibration point at which gaze data has not been acquired, the computational processing unit 230 instructs the marker control unit 220 to move the point-of-regard marker M to the next calibration point (S140). The marker control unit 220 outputs, to the eyewear terminal 100 via the transceiving unit 210, an instruction to move the point-of-regard marker M to the next preset calibration point.

(Point-of-Regard Marker Movement Process)

The point-of-regard marker M is displayed in order to direct the user's gaze. Herein, the display of the point-of-regard marker M is controlled to enable correct acquisition of the user's gaze data in a short time.

First, the point-of-regard marker M moves between respective calibration points while remaining displayed. As a result, the user's gaze moves to follow the point-of-regard marker, and compared to the case of intermittently displaying the point-of-regard marker M, time to search for the point-of-regard marker M displayed at a calibration point becomes unnecessary, and the movement of the gaze directed at the point-of-regard marker may be stabilized.

Additionally, the movement speed of the point-of-regard marker M moving between the calibration points is varied. If the point-of-regard marker M is moved at a constant speed, there is a tendency for the gaze to be less likely to settle when the point-of-regard marker M is displayed at the destination calibration point. Accordingly, the marker control unit 220 controls the movement speed of the point-of-regard marker M moving between calibration points to slow down as the point-of-regard marker M approaches the destination calibration point. Consequently, the point-of-regard marker M moves quickly immediately after the start of movement, but slows down as the point-of-regard marker M approaches the destination calibration point. Since the user's gaze moves along with the movement speed of the point-of-regard marker, the movement of the user's gaze also relaxes as the point-of-regard marker M approaches the destination calibration point, and the gaze settles down more easily when the point-of-regard marker M is displayed at the calibration point.

In addition, the calibration points at which to acquire gaze data in the display region 300 ordinarily are set in the center of the display region 300, which is the position that the user looks at when facing forward, and near the periphery of the display region 300, which is where the discrepancy between the sight axis and the optical axis tends to be larger. Ordinarily, multiple points (for example, from 5 to 9 points) inside the field of view are set as calibration points. By conducting calibration at these positions, a correction process may be conducted so that the appearance of the display region 300 becomes uniform overall. Specifically, as illustrated in FIG. 9, for example, calibration may be conducted in the center (calibration point CP1) and the four corners (calibration points CP2 to CP5) of a rectangular display region 300. Alternatively, as illustrated in FIG. 10, calibration may be conducted in the center (calibration point CP1) and near the midpoint of each edge (calibration points CP2 to CP5) of a rectangular display region 300.

At this point, when moving the point-of-regard marker M between respective calibration points, the movement sequence of the point-of-regard marker M may be decided so that the movement distance is as large as possible. The user moves his or her gaze along with the movement of the point-of-regard marker M, but if the movement distance of the point-of-regard marker M is small, the gaze is less likely to align with the point-of-regard marker M displayed at the next calibration point, and the discrepancy between the sight axis and the optical axis becomes larger. Also, since the discrepancy between the sight axis and the optical axis also tends to become larger when the point-of-regard marker M is moved in the horizontal direction of the display region 300, the point-of-regard marker M may also be moved so as to include movement in the vertical direction, such as moving up and down or diagonally.

For example, when acquiring gaze data at the five calibration points CP1 to CP5 set in the center and the four corners of the display region 300 illustrated in FIG. 9, after displaying the calibration point CP1 in the center, the calibration points CP2 to CP5 in the four corners may be moved to in a zigzag manner. Additionally, when acquiring gaze data at the five calibration points CP1 to CP5 set in the center and near the midpoint of each edge of the display region 300 illustrated in FIG. 10, for example, first, the calibration points CP1 to CP4 near the midpoint of each edge are displayed in a sequence so as to draw a diamond-shaped trail. After that, the calibration point CP1 in the center may be displayed.

Returning to the description of FIG. 5, after the point-of-regard marker M is moved to the next calibration point in step S140, the acquisition of gaze data at the destination calibration point is conducted (S110). After that, the processes from steps S110 to S140 are repeatedly executed until gaze data acquisition is completed at all calibration points.
(3) Evaluate (S150 to S180)

After gaze data is acquired at all calibration points, a calibration completion determination is made by the evaluation unit 250. In the present embodiment, the calibration completion determination is made by determining whether or not the overall variation in the estimated optical axis vectors vo is inside an allowed range.

After calibration is conducted correctly, the optical axis vectors vo at the respective calibration points computed in step S110 become values corresponding to the display positions of the calibration points in the display region 300. Herein, FIG. 11 illustrates an example of detection results for the optical axis vector vo when conducting calibration with the calibration points CP1 to CP5 illustrated in FIG. 9. FIG. 11 illustrates the relationship between the angle θ in the vertical direction of the optical axis vector vo, the angle w in the horizontal direction of the optical axis vector vo. Note that in the present embodiment, the optical axis vector vo is defined on the basis of the coordinate axes illustrated in FIG. 12. In the coordinate axes of FIG. 12, the x-axis represents the horizontal direction of the display region 300, the y-axis represents the vertical direction of the display region 300, and the z-axis represents the depth direction of the display region 300. The angle θ is the angle obtained between the optical axis vector vo and the zx plane, while the angle ω is the angle obtained between the optical axis vector vo and the xy plane.

The upper side of FIG. 11 illustrates a distribution of optical axis vectors vo when calibration is conducted correctly, while the lower side of FIG. 11 illustrates a distribution of optical axis vectors vo when calibration is not conducted correctly. According to the upper side of FIG. 11, when calibration is conducted correctly, the optical axis vectors vo are distributed with clean divisions in correspondence with each of the calibration points set in the center and the four corners of the display region 300.

On the other hand, as illustrated on the lower side of FIG. 11, when calibration is not conducted correctly, the optical axis vectors vo are not distributed cleanly. For example, the angle θ in the vertical direction of the optical axis vectors vo corresponding to the calibration points in the upper-right, the upper-left, and the center of the display region 300 become approximately the same. In particular, such a distribution occurs easily for the wearers of hard contact lenses or users with squinted, narrow eyes.

Accordingly, in the present embodiment, the evaluation unit 250 calculates a correlation relationship between the marker vector vm and the optical axis vector vo as an evaluation value for evaluating the overall variation in the optical axis vectors vo (S150), and makes the calibration completion determination from the value of the correlation relationship. A correlation coefficient $r_{xy}$ between the marker vector vm and the optical axis vector vo may be computed according to Formula (1) below, for example.

[Math. 1]

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \quad (1)$$

Note that i is a number assigned to each calibration point, and takes a value from 1 to n. When five calibration points are set, n is 5. Also, $x_i$ and $y_i$ are the x-coordinate and y-coordinate of the optical axis vector vo, while $\bar{x}$ and $\bar{y}$ are the x-coordinate and y-coordinate of the marker vector vm. Note that $\bar{x}$ and $\bar{y}$ herein denote that ¯ is appended above x and y.

In Formula (1) above, the difference between the angle θ in the vertical direction and the angle w in the horizontal direction for the marker vector vm and the optical axis vector vo at all calibration points is evaluated. If the marker vector vm and the optical axis vector vo do not match at one or multiple calibration points, and the discrepancy between these angles becomes large, the correlation coefficient $r_{xy}$ computed by Formula (1) becomes smaller. The evaluation unit 250 makes the calibration completion determination by using the correlation coefficient $r_{xy}$ expressing such a correlation relationship between the marker vector vm and the optical axis vector vo (S160).

The calibration completion determination may also be made in accordance with whether or not the correlation coefficient $r_{xy}$ between the marker vector vm and the optical axis vector vo computed in step S150 has fallen below a certain threshold $r_{th}$. The threshold $r_{th}$ may be set to 0.90, for example. In step S160, if the correlation coefficient $r_{xy}$ between the marker vector vm and the optical axis vector vo is greater than or equal to the threshold $r^{th}$, the evaluation unit 250 treats the overall variation of the optical axis vector vo as being inside the allowed range, and completes the calibration process (S170).

On the other hand, if the correlation coefficient $r_{xy}$ between the marker vector vm and the optical axis vector vo falls below the threshold $r^{th}$, the calibration settings information is modified to change how calibration is conducted (S180), and calibration is performed again. The calibration settings information refers to information such as the display position of the point-of-regard marker M, for example. For example, the calibration point settings may be modified to shift the display position of the point-of-regard marker M towards the center of the display region 300 or the like, and calibration may be executed again.

For example, as illustrated in FIG. 13, suppose that calibration points are set with respect to the display region 300 on the basis of a region obtained by reducing the display region 300 by a certain ratio a. At this point, suppose that the default values for the positions of the calibration points are the center of the display region 300, and the four corners of a region 90% the size of the display region, for example. When calibration is executed by setting the calibration points to the default positions, and the correlation coefficient $r_{xy}$ between the marker vector vm and the optical axis vector vo falls below the threshold $r^{th}$, the positions of the calibration points are shifted towards the center of the display region. For example, the positions of the calibration points in the four corners are set to the four corners of a region 80% the size of the display region. By shifting the positions of the calibration points towards the center of the display region in this way, the user becomes able to see the point-of-regard marker more easily, and correct gaze data may be acquired more easily.

The above thus describes the calibration process of the eyewear terminal 100 performed by the information processing apparatus 200 according to the present embodiment. According to the present embodiment, when acquiring gaze data at multiple calibration points, the point-of-regard marker M displayed to direct the user's gaze is moved to each calibration point while remaining displayed. At this time, the movement speed of the point-of-regard marker M may be slowed down as the point-of-regard marker M approaches the position of the next calibration point, thereby enabling the user's gaze to track the point-of-regard marker M accurately.

In addition, in the calibration process according to the present embodiment, when acquiring the optical axis vector vo at each calibration point, the presence or absence of divergence in the optical axis on the basis of previously acquired optical axis vectors may be determined, and the discrepancy between the marker vector vm and the optical axis vector vo may be determined. As a result, it is possible not to use gaze data acquired when the user is not looking at the point-of-regard marker M as a calibration detection result, and thereby not lower the accuracy of the gaze detection process.

Furthermore, in the calibration process according to the present embodiment, a correlation coefficient between the marker vector vm and the optical axis vector vo is computed from the optical axis vectors vo acquired at each calibration point as an evaluation value for evaluating the overall variation of the optical axis vector vo. By determining whether or not this relation coefficient is greater than or equal to a certain threshold value, it is possible to evaluate whether or not the gaze detection process may be conducted accurately inside the field of view as a whole. Consequently, no matter which position in the display region the user looks at, the accuracy of the detected optical axis vectors vo may be maintained consistently.

According to such a process, the calibration process may be completed simply by the user directing his or her gaze at the point-of-regard marker M. The point-of-regard marker M is displayed and moved to enable the user to direct his or her gaze easily. In addition, even if the optical axis vector vo is not acquired, the calibration points are adjusted automatically so that the optical axis vector vo may be acquired, and thus the calibration process may be completed without causing the user to feel stress.

<5. Adaptation to Detection Accuracy Improvement>

In the calibration process, variation in the detected optical axis vectors vo tends to occur in cases such as when the user is wearing hard contact lenses or when the user has narrow eyes. This is because when the user is wearing hard contact lenses, the pupil may be distorted, a number of bright points greater than the number of light sources may be detected on the eyeball due to light radiated from the light sources, or the contact lens may move over the cornea. Also, when the user has narrow eyes, the pupil specified from the captured image may be incomplete, or a number of bright points equal to the number of light sources which should be detected may not be detected. Accordingly, to detect the user's optical axis vector vo correctly, a process like the following may be conducted additionally.

[5.1. Pairing with Bright Points]

To detect the user's optical axis vector vo correctly, for example, a process of pairing bright points specified from the captured image may be conducted, for example. In the eyewear terminal 100 according to the present embodiment, as illustrated in FIG. 2, four light sources 103Ra to 103Rd and 103La to 103Ld are provided around the display units 102R and 102L, respectively. When the left and right eyes are respectively irradiated with light from these light sources 103Ra to 103Rd and 103La to 103Ld, the four bright points Pa, Pb, Pc, and Pd appear respectively in each eye, as illustrated in FIG. 14.

If the light sources 103Ra to 103Rd and 103La to 103Ld are arranged as illustrated in FIG. 2, the bright points Pa, Pb, Pc, and Pd corresponding to the arrangement are detected in each eye 10 by the light emitted from these light sources. However, as discussed earlier, when the user is wearing hard contact lenses or when the user has narrow eyes, more bright points than the four bright points Pa, Pb, Pc, and Pd may be detected, or the four bright points may not be detected.

Accordingly, the bright points Pa and Pc facing each other vertically, and the bright points Pb and Pd facing each other horizontally are treated as respective pairs. Subsequently, on the basis of the positional relationship of the light sources corresponding to the paired bright points, when one bright point is detected, it becomes possible to estimate the position of the other bright point. For example, if the bright point Pa is detected, even if the bright point Pc is not detected, it is possible to estimate that the bright point Pc exists at a certain position below the bright point Pa. Also, even if more bright points than the number of light sources are detected, on the basis of the positional relationship of the light sources corresponding to the bright points, it is possible to specify the paired bright points from among many detected bright points.

In this way, by setting pairs of bright points from the arrangement of the light sources, it becomes possible to estimate the approximate positions of the bright points even if a bright point is not correctly detected from the captured image, and the detection accuracy of the optical axis vector vo may be improved.

[5.2. Dynamic Change of Point-of-Regard Marker Display Position]

In addition, to detect the user's optical axis vector vo correctly, the point-of-regard marker M may also be moved dynamically. When the point-of-regard marker M is displayed at a position in the display region 300 that is difficult for the user to direct his or her gaze at, it is anticipated that the detected optical axis vector vo will be more greatly divergent from the marker vector vm. In such cases, even if the point-of-regard marker M continues to be displayed at the same calibration point, the discrepancy between the optical axis vector vo and the marker vector vm will not become smaller.

Accordingly, if the optical axis vector vo at such a calibration point cannot be acquired within a certain amount of time, for example, the display position of the point-of-regard marker M is shifted towards the center of the display region 300, and the process of acquiring the optical axis vector vo is executed again. The time at which to move the point-of-regard marker M may be a time such as after the elapse of a few seconds (for example, 3 seconds) from when the point-of-regard marker M is displayed at the calibration point, for example.

The movement of the point-of-regard marker M may approach the center of the display region 300 by a certain ratio with respect to the distance from the center of the display region 300 to the current calibration point, for example. Alternatively, the movement of the point-of-regard marker M may approach the middle of the display region 300 in the horizontal direction by a certain ratio with respect to the horizontal distance from the horizontal middle of the display region 300 to the current calibration point, for example. The certain ratio of approach by the point-of-regard marker M may be set to approximately 10%, for example. Consequently, the distance over which the user moves his or her gaze from a state of facing forward becomes smaller, thereby making it easier for the user to direct his or her at the point-of-regard marker M. Thus, a smaller discrepancy between the optical axis vector vo and the marker vector vm may be expected.

The movement of the point-of-regard marker M may also be performed until the optical axis vector vo is acquired, for example. For example, if the acquisition of the optical axis vector vo is conducted for a certain time, but the optical axis vector vo is not acquired within that time, the process may be repeated by which the point-of-regard marker M is additionally moved by the certain ratio, and the acquisition of the optical axis vector vo is conducted again. Subsequently, when the optical axis vector vo is acquired, for example, during the acquisition of the optical axis vector vo at subsequent calibration points, the point-of-regard marker M may be displayed at the positions obtained by moving the positions of the calibration points by the certain ratio used when acquiring the current optical axis vector vo. Obviously, during the acquisition of the optical axis vector vo at subsequent calibration points, the point-of-regard marker M may also be displayed at the default positions of the calibration points.

In this way, when the acquisition of the optical axis vector vo is unsuccessful, by dynamically moving the point-of-regard marker M to a position where the optical axis vector vo is acquired correctly, the correct optical axis vector vo may be acquired.

<6. Hardware Configuration Example>

Finally, an exemplary hardware configuration of the information processing apparatus 200 according to the present embodiment will be described. FIG. 15 is a hardware block diagram illustrating an exemplary hardware configuration of the information processing apparatus 200 according to the present embodiment.

As described above, the information processing apparatus 200 according to the embodiments can be implemented as a processing device such as a computer. As illustrated in FIG. 15, the information processing apparatus 200 includes a central processing unit (CPU) 901, read only memory (ROM) 902, random access memory (RAM) 903, and a host bus 904a. Furthermore, the information processing apparatus 200 includes a bridge 904, an external bus 904b, an interface 905, an input device 906, an output device 907, a storage device 908, a drive 909, a connection port 911, and a communication device 913.

The CPU 901 functions as an arithmetic processing unit and a controller, and controls the overall operation in the information processing apparatus 200 according to various programs. Furthermore, the CPU 901 may be a microprocessor. The ROM 902 stores programs, operation parameters, and the like that the CPU 901 uses. The RAM 903 temporarily stores programs used in the execution of the CPU 901 and the parameters and the like that appropriately changes during the execution. The above are interconnected via a host bus 904a constituted by a CPU bus.

The host bus 904a is connected to the external bus 904b, such as a peripheral component interconnect/interface (PCI) bus, through the bridge 904. Note that the host bus 904a, the bridge 904, and the external bus 904b are not necessarily configured as separate components but the functions thereof may be implemented in a single bus.

The input device 906 includes input devices for the user to input information, such as a mouse, a keyboard, a touch panel, a button, a microphone, a switch, and a lever, and an input control circuit that generates an input signal on the basis of the input performed by the user and that outputs the input signal to the CPU 901. The output device 907 includes, for example, a display device, such as a liquid crystal display (LCD) device, an organic light emitting diode (OLED) device, or a lamp, and speech output device, such as a speaker.

The storage device 908 is an example of the storage unit of the information processing apparatus 200 and is a device for storing data. The storage device 908 may include a recording medium, a recording device that records data in the recording medium, a readout device that reads out data from the recording medium, and a deletion device that deletes data recoded in the recording medium. The storage device 908 drives the hard disk and stores therein programs that the CPU 901 executes and various kinds of data.

The drive 909 is a reader/writer for a recording medium and is built-in the information processing apparatus 200 or is externally attached. The driver 909 reads out information recorded in a magnetic disk, an optical disk, or a magneto-optical disc that is mounted thereto or a removable storage medium such as a semiconductor memory and outputs the information to the RAM 903.

The connection port 911 is an interface connected to an external device and is a port for connecting an external device that is capable of data transmission through, for example, a universal serial bus (USB). Furthermore, the communication device 913 is a communication interface constituted by, for example, a communication device or the like for connecting to a communication network. Furthermore, the communication device 913 may be a communication device corresponding to a local area network (LAN), a communication device corresponding to a wireless USB, or a wired communication device that communicates through wire.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the foregoing embodiment, if the correlation coefficient $r_{xy}$ between the marker vector vm and the optical axis vector vo falls below the threshold $r^{th}$, the method of calibration is changed and calibration is performed again, but the present technology is not limited to such an example. For example, before changing the method of calibration, the threshold $r^{th}$ may be lowered, and the calibration completion determination may be made again.

The changed threshold $r^{th}$ may be a value obtained by lowering the previous threshold $r^{th}$ by a fixed value, or a value between the correlation coefficient $r_{xy}$ and the previous threshold $r^{th}$, for example. Additionally, calibration may be ended, and calibration may be conducted again using calibration information from when the threshold $r^{th}$ was highest previously.

Further, the effects described in this specification are merely illustrative or exemplified effects, and are not limitative. That is, with or in the place of the above effects, the technology according to the present disclosure may achieve other effects that are clear to those skilled in the art based on the description of this specification. Additionally, the present technology may also be configured as below.

(1)

An information processing apparatus, including:

a marker control unit that changes, during calibration of an eyewear terminal, a display position of a point-of-regard marker displayed on a display unit of the eyewear terminal;

a computational processing unit that computes an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and an evaluation unit that evaluates a variation of the optical axis vector computed for a plurality of the calibration points.

(2)

The information processing apparatus according to (1), wherein the marker control unit moves the point-of-regard marker to the calibration points in a preset sequence while keeping the point-of-regard marker displayed.

(3)

The information processing apparatus according to (2), wherein the marker control unit moves the point-of-regard marker so that a movement speed slows down as the point-of-regard marker approaches a destination calibration point.

(4)

The information processing apparatus according to any one of (1) to (3), wherein the computational processing unit determines whether an angle obtained between a currently computed optical axis vector and an average of the optical axis vector computed on a basis of a history of optical axis vectors is greater than a certain angle, and if the obtained angle is greater than the certain angle, the computational processing unit does not adopt the currently computed optical axis vector.

(5)

The information processing apparatus according to any one of (1) to (4), wherein the computational processing unit determines a variation of a currently computed optical axis vector on a basis of whether an angle obtained between the currently computed optical axis vector and a marker vector from a pupil center of the user to the calibration point where the point-of-regard marker is displayed is less than or equal to a certain angle, and if the obtained angle is greater than the certain angle, the computational processing unit does not adopt the currently computed optical axis vector.

(6)

The information processing apparatus according to (5), wherein the computational processing unit does not adopt the computed optical axis vector when a size ratio of left and right pupils of the user is greater than or equal to a certain value.

(7)

The information processing apparatus according to any one of (4) to (6), wherein when the optical axis vector computed by the computational processing unit is not adopted, the marker control unit moves the display position of the point-of-regard marker towards a center of a display region.

(8)

The information processing apparatus according to any one of (1) to (7), wherein the evaluation unit determines the variation of the optical axis vector computed at all of the calibration points, on a basis of a correlation relationship between a marker vector from a pupil center of the user to the calibration point where the point-of-regard marker is displayed and the computed optical axis vector.

(9)

The information processing apparatus according to (8), wherein when the evaluation unit determines that a correlation coefficient expressing the correlation relationship between the optical axis vector and the marker vector has fallen below a certain threshold, the marker control unit sets the calibration point to a position shifted towards a center of a display region, and executes calibration again.

(10)

The information processing apparatus according to any one of (1) to (9), wherein the computational processing unit detects bright points due to light radiated from a plurality of paired light sources.

(11)

An information processing method, conducted by an information processing apparatus, the method including:

changing, during calibration of an eyewear terminal, a display position of a point-of-regard marker displayed on a display unit of the eyewear terminal;

computing an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and evaluating a variation of the optical axis vector computed for a plurality of the calibration points.

(12)

A program causing a computer to function as an information processing apparatus including:

a marker control unit that changes, during calibration of an eyewear terminal, a display position of a point-of-regard marker displayed on a display unit of the eyewear terminal;

a computational processing unit that computes an optical axis vector expressing a gaze direction of a user by a pupil-corneal reflection method, on a basis of a captured image that includes a user's eye imaged when the eye of the user wearing the eyewear terminal is irradiated with light from a light source, and the point-of-regard marker is displayed at a calibration point; and an evaluation unit that evaluates a variation of the optical axis vector computed for a plurality of the calibration points.

REFERENCE SIGNS LIST

10 eye
14 cornea 17 pupil
100 eyewear terminal
110 light source
120 imaging unit
130 display unit
140 control unit
150 transceiving unit
200 information processing apparatus
210 transceiving unit
220 marker control unit
230 computational processing unit
240 storage unit
250 evaluation unit
300 display region

The invention claimed is:

1. An information processing apparatus, comprising:
   circuitry configured to:
   control a display screen of a mobile terminal to display a marker image at a first position in a first corner region of the display screen;
   control a light source of the mobile terminal to irradiate an eye of a user with infrared light;
   control an imaging unit of the mobile terminal to acquire a first captured image of the eye of the user while the light source irradiates the eye of the user and the marker image is displayed at the first position;
   determine a correlation coefficient that represents correlation between an optical axis vector and a marker vector, wherein
     the optical axis vector corresponds to a gaze direction of the user,
     the marker vector corresponds to a vector that connects a position of the marker image with a position of the eye, and
     the correlation coefficient is based on a difference between x-coordinates of the optical axis vector and x-coordinates of the marker vector and a difference between y-coordinates of the optical axis vector and y-coordinates of the marker vector;
   determine first acquisition of the optical axis vector as a success based on the correlation coefficient associated with the first captured image is greater than or equal to a threshold value;
   determine the first acquisition of the optical axis vector as a failure based on the correlation coefficient associated with the first captured image is less than the threshold value;
   control, based on the determination that the first acquisition of the optical axis vector is a failure, the display screen to move the marker image from the first position to a second position in the first corner region, wherein
     the second position in the first corner region is closer to a center of the display screen than the first position,
     a distance between the second position in the first corner region and the first position in the first corner region is lesser than a distance between the second position and the center of the display screen, and
     the first corner region is different from a specific region that includes the center of the display screen;
   control the imaging unit to acquire a second captured image of the eye of the user while the light source irradiates the eye of the user and the marker image is displayed at the second position;
   determine second acquisition of the optical axis vector as a success or a failure based on the correlation coefficient associated with the second captured image; and
   calibrate gaze detection based on the determination that the second acquisition of the optical axis vector succeeds.

2. The information processing apparatus according to claim 1, wherein
   the circuitry is configured to:
   control, based on the determination that the first acquisition of the optical axis vector is a success, the display screen to move the marker image from the first position to a third position in a second corner region of the display screen, wherein the second corner region is different from the first corner region;
   control the imaging unit of the mobile terminal to acquire a third captured image of the eye of the user while the light source irradiates the eye of the user and the marker image is displayed at the third position;
   determine whether third acquisition of the optical axis vector succeeds based on the third captured image;
   control, based on the determination that the second acquisition of the optical axis vector is a success, the display screen to move the marker image from the second position to a fourth position of the display screen in the second corner region, wherein the fourth position is closer to the center of the display screen than the third position;
   control the imaging unit to acquire a fourth captured image of the eye of the user while the light source irradiates the eye of the user and the marker image is displayed at the fourth position;
   determine whether fourth acquisition of the optical axis vector succeeds based on the fourth captured image; and
   calibrate the gaze detection based on a successful combination of the first acquisition and the third acquisition of the optical axis vector or a successful combination of the second acquisition and the fourth acquisition of the optical axis vector.

3. The information processing apparatus according to claim 2, wherein the first corner region is opposite to the second corner region.

4. The information processing apparatus according to claim 1, wherein the circuitry is configured to control, based on the determination that the first acquisition of the optical axis vector is a failure, the display screen to move the marker image from the first position in a horizontal direction of the display screen.

5. The information processing apparatus according to claim 1, wherein the circuitry is configured to:
   control, based on the determination that the first acquisition of the optical axis vector is a success, the display screen to move the marker image from the first position to a third position in a second corner region of the display screen, wherein the second corner region is different from the first corner region; and
   decrease a movement speed of the marker image as the marker image approaches the third position.

6. The information processing apparatus according to claim 5, wherein the first corner region is opposite to the second corner region.

7. The information processing apparatus according to claim 1, wherein the mobile terminal is a head-mounted display.

8. An information processing method, comprising:
controlling a display screen of a mobile terminal to display a marker image at a first position in a corner region of the display screen;
controlling a light source of the mobile terminal to irradiate an eye of a user with infrared light;
controlling an imaging unit of the mobile terminal to acquire a first captured image of the eye of the user while the light source irradiates the eye of the user and the marker image is displayed at the first position;
determining a correlation coefficient that represents a correlation between an optical axis vector and a marker vector, wherein
the optical axis vector corresponds to a gaze direction of the user,
the marker vector corresponds to a vector that connects a position of the marker image with a position of the eye, and
the correlation coefficient is based on a difference between x-coordinates of the optical axis vector and x-coordinates of the marker vector and a difference between y-coordinates of the optical axis vector and y-coordinates of the marker vector;
determining first acquisition of the optical axis vector as a success based on the correlation coefficient associated with the first captured image is greater than or equal to a threshold value;
determining the first acquisition of the optical axis vector as a failure based on the correlation coefficient associated with the first captured image is less than the threshold value:
controlling, based on the determination that the first acquisition of the optical axis vector is a failure, the display screen to move the marker image from the first position to a second position in the corner region, wherein
the second position in the corner region is closer to a center of the display screen than the first position,
a distance between the second position in the corner region and the first position in the corner region is lesser than a distance between the second position and the center of the display screen, and
the corner region is different from a specific region that includes the center of the display screen;
controlling the imaging unit to acquire a second captured image of the eye of the user while the light source irradiates the eye of the user and the marker image is displayed at the second position;
determining second acquisition of the optical axis vector as a success or a failure based on the correlation coefficient associated with the second captured image; and
calibrating gaze detection based on the determination that the second acquisition of the optical axis vector succeeds.

9. A non-transitory computer-readable medium having stored thereon, computer-executable instructions, which when executed by a processor of an information processing apparatus, cause the processor to execute operations, the operations comprising:
controlling a display screen of a mobile terminal to display a marker image at a first position in a corner region of the display screen;
controlling a light source of the mobile terminal to irradiate an eye of a user with infrared light;
controlling an imaging unit of the mobile terminal to acquire a first captured image of the eye of the user while the light source irradiates the eye of the user and the marker image is displayed at the first position;
determining a correlation coefficient that represents a correlation between an optical axis vector and a marker vector, wherein
the optical axis vector corresponds to a gaze direction of the user,
the marker vector corresponds to a vector that connects a position of the marker image with a position of the eye, and
the correlation coefficient is based on a difference between x-coordinates of the optical axis vector and x-coordinates of the marker vector and a difference between y-coordinates of the optical axis vector and y-coordinates of the marker vector;
determining first acquisition of the optical axis vector as a success based on the correlation coefficient associated with the first captured image is greater than or equal to a threshold value;
determining the first acquisition of the optical axis vector as a failure based on the correlation coefficient associated with the first captured image is less than the threshold value:
controlling, based on the determination that the first acquisition of the optical axis vector is a failure, the display screen to move the marker image from the first position to a second position in the corner region, wherein
the second position is closer to a center of the display screen than the first position,
a distance between the second position in the corner region and the first position in the corner region is lesser than a distance between the second position and the center of the display screen, and
the corner region is different from a specific region that includes the center of the display screen;
controlling the imaging unit to acquire a second captured image of the eye of the user while the light source irradiates the eye of the user and the marker image is displayed at the second position;
determining second acquisition of the optical axis vector as a success or a failure based on the correlation coefficient associated with the second captured image; and
calibrating gaze detection based on the determination that the second acquisition of the optical axis vector succeeds.

* * * * *